United States Patent [19]

Aoki et al.

[11] 4,275,078
[45] Jun. 23, 1981

[54] N-BENZOYL-N'-HALOGENOALK-YLIDENEHYDRAZINE DERIVATIVES, PROCESS FOR PREPARING SAME, AND AGRICULTURAL AND HORTICULTURAL FUNGICIDE COMPRISING SUCH DERIVATIVES

[75] Inventors: Katsumichi Aoki; Takafumi Shida; Satoru Kumazawa; Masashi Ohtsuru; Shiro Yamazaki, all of Iwaki, Japan

[73] Assignee: Kureha Kagaku Kogyo Kabushiki Kaisha, Tokyo, Japan

[21] Appl. No.: 29,010

[22] Filed: Apr. 11, 1979

[30] Foreign Application Priority Data

Apr. 24, 1978 [JP] Japan .................................. 53-48493

[51] Int. Cl.³ ...................... C07C 109/18; A01N 9/20
[52] U.S. Cl. .................................... 424/324; 564/149
[58] Field of Search ..................... 260/558 H; 424/324

[56] References Cited

U.S. PATENT DOCUMENTS

| | | | |
|---|---|---|---|
| 2,767,173 | 10/1956 | Katz | 260/558 H X |
| 3,285,929 | 11/1966 | Klauke et al. | 260/551 S X |
| 3,836,580 | 9/1974 | Bruce | 260/558 H |
| 3,860,589 | 1/1975 | Pilgrim et al. | 260/241 |
| 3,886,211 | 5/1975 | Keenan | 260/558 H X |
| 4,071,633 | 1/1978 | Aoki et al. | 260/558 H X |
| 4,166,129 | 8/1979 | Aoki et al. | 260/558 H X |

FOREIGN PATENT DOCUMENTS

| | | |
|---|---|---|
| 659441 | 3/1963 | Canada. |
| 1022218 | 1/1958 | Fed. Rep. of Germany ...... 260/558 H |
| 2369254 | 5/1978 | France ........................... 564/149 |

OTHER PUBLICATIONS

Kametani et al., CA 62: 16110g (1965),. J. Pharm. Soc. Japan, vol. 85 (1965).
Kametani et al., "Chemical Abstracts", vol. 60, Ab. No. 15772b, (1964).
Houben-Weyl, V/16, pp. 9-11, (1972).
Houben-Weyl, V/3, pp. 813-815 (1962).
Gillis et al., "The Journal of Organic Chemistry", vol. 32(1), pp. 91-94, (1967).

*Primary Examiner*—John Doll
*Attorney, Agent, or Firm*—Wegner & Bretschneider

[57] ABSTRACT

Novel N-benzoly-N'-halogenoloweralkylidenehydrazine derivatives of the general formula

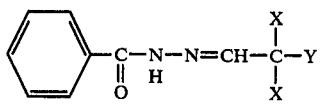

(in which X represents Cl or Br, and Y represents H, F, Cl, Br, CH$_3$ or CHCl—CH$_3$, provided that when X is Cl, Y is the above-defined member other than Cl).

2 Claims, No Drawings

N-BENZOYL-N'-HALOGENOALKYLIDENEHYDRAZINE DERIVATIVES, PROCESS FOR PREPARING SAME, AND AGRICULTURAL AND HORTICULTURAL FUNGICIDE COMPRISING SUCH DERIVATIVES

This invention relates to novel derivatives of N-benzoyl-N'-halogenoalkylidenehydrazine represented by the following general formula (I), their preparation and an agricultural or horticultural fungicide comprising these derivatives

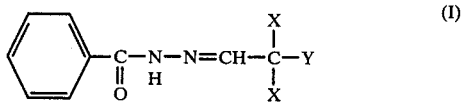

(in which X represents Cl or Br, and Y represents H, F, Cl, Br, $CH_3$ or $CHClCH_3$, provided that when X is Cl, Y is the member other than Cl).

Heretofore, there have been known a great number of compounds using substituted benzoylhydrazine. Some compounds are also known of reaction products of benzoylhydrazine and halogenoalkanals. For instance, N-benzoyl-N'-trichloroethylidenehydrazine is described in The Journal of the Pharmaceutical Society of Japan 85, (3) 181 (1965). N-benzoyl-N'-trifluoroethylidenehydrazine has been reported in Chemical Abstracts 82, 112112n (1975). However, these reports are both directed to only the reactions to prepare the compounds but do not refer at all to their antifungal action useful as a pesticide or fungicide for agriculture or horticulture.

We have synthesized novel derivatives of N-benzoyl-N'-halogenoalkylidenehydrazine and, as a result of wide screening, found that these derivatives show an excellent efficacy as the agricultural and horticultural fungicide. The present invention is accomplished on the basis of the above finding.

Typical examples of the compounds according to the present invention are tabulated in the following Table 1.

TABLE 1

| Compound No. | Structural Formula | Name | Melting Point | Yield |
|---|---|---|---|---|
| 1 | Ph-C(=O)-N(H)-N=CH-CBr₃ | N-benzoyl-N'-(2,2,2-tribromoethylidene)hydrazine | 168°–9° C. (decomposed) | 91% |
| 2 | Ph-C(=O)-N(H)-N=CH-CBr₂Cl | N-benzoyl-N'-(2,2-dibromo-2-chloroethylidene)hydrazine | 178° C. (decomposed) | 57% |
| 3 | Ph-C(=O)-N(H)-N=CH-CCl₂F | N-benzoyl-N'-(2,2-dichloro-2-fluoroethylidene)hydrazine | 170°–1° C. (decomposed) | 8.4% |
| 4 | Ph-C(=O)-N(H)-N=CH-CCl₂Br | N-benzoyl-N'-(2-bromo-2,2-dichloroethylidene)hydrazine | 184° C. (decomposed) | 99% |
| 5 | Ph-C(=O)-N(H)-N=CH-CCl₂H | N-benzoyl-N'-(2,2-dichloroethylidene)hydrazine | 150°–1° C. (decomposed) | 50% |
| 6 | Ph-C(=O)-N(H)-N=CH-CCl₂-CH₃ | N-benzoyl-N'-(2,2-dichloropropylidene)hydrazine | 243°–4° C. (decomposed) | 10% |
| 7 | Ph-C(=O)-N(H)-N=CH-CCl₂-CHCl-CH₃ | N-benzoyl-N'-(2,2,3-trichlorobutylidene)hydrazine | 153°–4° C. (decomposed) | 82% |

The compounds according to the present invention can be prepared, for example, by the following two methods.

The first method is carried out according to the following reaction formula and is a basically known one:

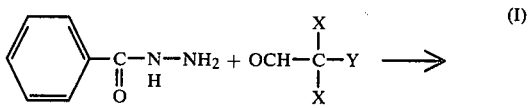

That is, the derivatives can be readily obtained by interacting benzoylhydrazine and corresponding halogenoalkanals or acetals thereof either in benzene under reflux or in acetic acid at room temperature.

The second method makes use of a new reaction found by the inventors and has an advantage in a case where the first method cannot be employed because a halogenoacetaldehyde is of the type which is hard to obtain. The reaction is feasible as follows:

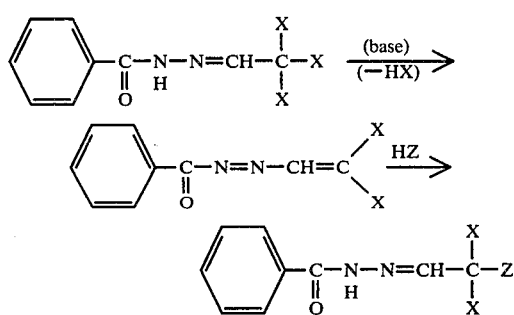

(in which X represents Cl or Br and Z represents F, Cl or Br). That is, a compound serving as a base, e.g. potassium acetate, sodium formate or triethylamine, is brought to reaction with the N-benzoyl-N'-trihalogenoethylidenehydrazine expressed by the general formula (II) to give a dehydrohalogenated product (1-benzoylazo-2,2-dihalogenoethylene expressed by the general formula (III)), followed by addition reacting with a hydrogen halide (H—Z) different from the hydrogen halide released on the dehalogenation reaction to obtain the product of the general formula (IV).

The synthesis will be particularly illustrated by the following Synthetic Examples.

SYNTHETIC EXAMPLE 1

Synthesis of N-benzoyl-N'-(2,2,2-tribromoethylidene)hydrazine (Compound No. 1)

1.4 g of benzoylhydrazine and 4.2 g of bromal were added to 20 ml of benzene, followed by refluxing for 3 hours. After allowing to cool, the precipitated crystals were collected by filtration and recrystallized from acetone.

Yield: 3.6 g (91% of the theoretical).
M.P.: 168°–9° C. (decomposed).
IR (KBr): 3160, 3020, 1650 cm$^{-1}$.

SYNTHETIC EXAMPLE 2

Synthesis of N-benzoyl-N'-(2,2,3-trichlorobutylidene)hydrazine (Compound No. 7)

1.4 g of benzoylhydrazine and 2.6 g of 2,2,3-trichlorobutylaldehyde were added to 20 ml of benzene and refluxed for 3 hours.

Yield: 2.4 g (82% of the theoretical).
M.P.: 153°–4° C. (decomposed).
IR (KBr): 3200, 3050, 1655 cm$^{-1}$.

SYNTHETIC EXAMPLE 3

Synthesis of N-benzoyl-N'-(2,2-dichloro-ethylidene) hydrazine (Compound No. 5)

14 g of N-benzoyl-N'-(2,2,2-trichloroethylidene) hydrazine was dissolved in 350 ml of acetone, to which was added 5.0 g of sodium formate, followed by stirring at room temperature for 2 hours to obtain a red reaction mixture. The acetone was distilled off under reduced pressure and the residue was subjected to extraction with benzene. The benzene layer was washed with water, dried and subjected to distillation to remove the solvent to obtain 9.7 g of dark red, oily 1-benzoylazo-2,2-dichloroethylene (at 80% of the theoretical).

This substance has a boiling point of 144°–6° C. (5.5 mmHg), was distillable, and was crystallized in the form of dark red plate crystals with a melting point of 50°–1° C.

IR (liquid film): 1710 cm$^{-1}$.
MS:M+m/e 228 (2-Cl).
NMR (CCl$_4$): δ (ppm), 6.85–7.20 (3H.m), 7.0 (1H.S), 7.20–7.65 (2H,m).

Elementary Analysis: Found:C 47.6%, H 2.6%, N 12.2%, Cl 30.6%. Calculated for C$_9$H$_6$Cl$_2$N$_2$O: C 47.3%, H 2.6%, N 12.2%, Cl 30.7%.

When a 10% aqueous hydrobromic acid solution was added to 406 mg of the thus obtained benzoylazodichloroethylene, the red color of the substance was immediately faded with the attendant precipitation of white crystals. The crystals were collected by filtration and washed with water to obtain the compound No. 4.

Yield: 542 mg (99% of the theoretical).
M.P.: 184° C. (decomposed).
IR (KBr): 3200, 3000, 1655 cm$^{-1}$.

SYNTHETIC EXAMPLE 4

Synthesis of N-benzoyl-N'-(2,2-dichloro-2-fluoroethylidene) hydrazine (Compound No. 3)

To 1.53 g of 1-benzoylazo-2,2-dichloroethylene obtained by the reaction as shown in Synthetic Example 3 was added 25 ml of 48% hydrofluoric acid at room temperature, followed by stirring for 30 minutes. The resulting crystals were collected by filtration and washed with water to obtain 1.23 g of crude crystals. The crude product which was contaminated with N-benzoyl-N'-(2,2,2-trichloroethylidene) hydrazine was treated with sodium formate to remove the contaminant as 1-benzoylazo-2,2-dichloroethylene and was then recrystallized from benzene.

Yield: 0.14 g (84% of the theoretical).
M.P.: 170°–1° C. (decomposed)
IR (KBr): 3200, 3050, 1660 980 cm$^{-1}$

SYNTHETIC EXAMPLE 5

Synthesis of N-benzoyl-N'-(2,2-dibromo-2-chloroethylidene) hydrazine (Compound No. 2)

3.0 g of N-benzoyl-N'-(2,2,2-tribromoethylidene) hydrazine (Compound No. 1) was dissolved in 100 ml of acetone, to which was further added 1.0 g of sodium formate, followed by stirring at room temperature for 1 hour. The insoluble salts were removed by filtration and the acetone was distilled off to obtain dark red, oily 1-benzoylazo-2,2-dibromoethylene.

Yield: 2.1 g (89% of the theoretical).
IR (liquid film): 1710 cm$^{-1}$.

To 1.5 g of the thus obtained benzoylazodibromoethylene was added 25 ml of a 36% aqueous hydrochloric acid solution for reaction at room temperature. The resulting white crystals were collected by filtration and recrystallized from acetone to obtain the Compound No. 2.

Yield: 0.95 g (57% of the theoretical).
M.P.: 178° C. (decomposed).
IR (KBr): 3200, 3050, 1655 cm$^{-1}$.

Those compounds obtained by Synthetic Examples may be conveniently used as they are or in the form of a dust, wettable powder, emulsion or liquid by mixing with suitable carrier (diluent).

As a matter of course, when applied as the plant disease-controlling agent for agriculture or horticulture, the compounds according to the invention may be, if required, admixed with any suitable additives such as a spreader, emulsifier, wettable agent, adhesive agent and the like to ensure the effect of the agent.

The compound or agent may be used in combination with or by mixing with other fungicides, insecticides or fertilizers since it shows no tendency of undergoing any decomposition or modification thereby or of decomposing or modifying other components.

The following examples illustrate the invention but should not be construed as limitation of the invention since the kinds of carrier (diluent) and additives, their mixing ratios and effective components may be further changed or modified without departing from the scope and spirit of the invention.

EXAMPLE 1

Dust:

| Compound No. 1 | 3 parts (by weight) |
| Talc | 40 parts |
| | 57 parts |

The composition of the above formulation was mixed and powdered, which was usable by dusting.

EXAMPLE 2

Wettable Powder:

| Compound No. 2 | 50 parts (by weight) |
| Sodium alkylnaphthalenesulfonic acid | 3 parts |
| Sodium ligninsulfonic acid | 4 parts |
| Diatomaceous earth | 43 parts |

The composition of the above formulation was mixed and powdered, which was used as a wettable powder by dilution with water.

Finally, there are described biological experimental examples showing the excellent fungicidal efficacy of the compounds according to the invention.

EXPERIMENTAL EXAMPLE 1

Test for Effect of Controlling Rice Blast (*Pyricularia oryzae*) by Pot Test

A wettable powder, as obtained in Example 2, diluted with and suspended in water in a predetermined concentration was sprayed over seedlings of rice plant (variety: Sasanishiki) of the four-leaf-stage cultivated in unglazed pots of 10 cm in diameter such that the leaves were adequately wetted with the suspension. After drying the leaves, a suspension of spores of *Pyricularia oryzae* was inoculated by spraying and the inoculated seedlings were held under high humidity conditions at 27°–28° C. Four days after the inoculation, the number of lesions on the leaves were checked on the following standard basis:

One top leaf/seedling, 20 seedlings/pot and 3 pots/treatment.

The disease inhibiting rate was calculated as follows:

Inhibiting Rate (%) =
$$(1 - \frac{\text{the total number of lesions on treated leaves}}{\text{the total number of lesions on non-treated leaves}}) \times 100$$

The results are shown in Table 2.

TABLE 2

| Tested Compound No. | Concentration (ppm) | The total number of lesions | Disease inhibiting rate (%) | Phytotoxicity |
|---|---|---|---|---|
| 1 | 500 | 16 | 98.1 | nil |
| 2 | " | 0 | 100 | " |
| 3 | " | 0 | 100 | " |
| 4 | " | 19 | 97.7 | " |
| 5 | " | 0 | 100 | " |
| 6 | " | 86 | 89.7 | " |
| 7 | " | 27 | 96.8 | " |
| non-treated | — | 835 | — | — |

EXPERIMENTAL EXAMPLE 2

Test for Effect of Controlling Helminthosporium Leaf Spot (*Cochliobolus miyabeanus*) on Rice Plant by Pot Test A wettable powder as obtained in Example 2 was diluted with and suspended in water in a predetermined concentration and sprayed over young seedlings of aquatic rice plant of the four-leaf-stage cultivated in unglazed pots of 10 cm in diameter so that the leaves were adequately wetted with the suspension. After drying the leaves, a suspension of spores of *Cochliobolus miyabeanus* was inoculated by spraying and the inoculated seedlings were maintained under high humidity conditions at 27°–28° C. Four days after the inoculation, the number of lesions were checked with the leaves as follows:

One top leaf/seedling, 20 seedlings/pot and 3 pots/treatment.

The disease inhibiting rate was calculated from the following equation:

Inhibiting Rate (%) =
$$(1 - \frac{\text{the total number of lesions on treated leaves}}{\text{the total number of lesions on non-treated leaves}}) \times 100$$

The test results are shown in Table 3 below.

TABLE 3

| Tested Compound No. | Concentration (ppm) | The total number of lesions | Disease inhibiting rate (%) | Phytotoxicity |
|---|---|---|---|---|
| 1 | 500 | 25 | 97.6 | nil |
| 2 | " | 0 | 100 | " |
| 3 | " | 0 | 100 | " |
| 4 | " | 37 | 96.5 | " |
| 5 | " | 0 | 100 | " |
| 6 | " | 58 | 94.5 | " |
| 7 | " | 28 | 97.4 | " |
| non-treated | — | 1065 | — | — |

EXPERIMENTAL EXAMPLE 3

Test for Effect of Controlling Downy Mildew (*Pseudoperonospora cubensis*) on Cucumber A wettable powder as obtained in Example 2 was diluted with and suspended in water in a predetermined concentration and sprayed over cucumber plants of the two-leaf-stage (variety: Sagami Hanjiro, one plant/pot, 3 pots/treated plot) cultivated in unglazed pots of 10 cm in diameter. After drying the sprayed leaves, a suspension of spores of *Pseudoperonospora cubensis* obtained by washing the inoculated cucumber leaves with distilled water was inoculated by spraying, followed by maintaining under high humidity conditions at 22°-23° C. for 24 hours and then allowing to stand in a greenhouse. Five days after the inoculation, the leaves were checked to determine an average degree of infection per leaf with regard to one leaf/pot and 3 pots/treated plot on the following standard basis.

Check Standard:

| Degree of Infection | Degree of Disease |
| --- | --- |
| 0 | Not infected at all. |
| 0.5 | Infected to less than 10% of the surface area of inoculated leaf. |
| 1 | Infected to 10-20% of the surface area of inoculated leaf. |
| 2 | Infected to 20-40% of the surface area of inoculated leaf. |
| 3 | Infected to 40-60% of the surface area of inoculated leaf. |
| 4 | Infected to 60-80% of the surface area of inoculated leaf. |
| 5 | Infected to more than 80% of the surface area of inoculated leaf |

The test results are shown in Table 4 below.

TABLE 4

| Tested Compound No. | Concentration (ppm) | Average Degree of Infection | Phytotoxicity |
| --- | --- | --- | --- |
| 1 | 500 | 0 | nil |
| 2 | " | 0 | " |
| 3 | " | 0 | " |
| 4 | " | 0 | " |
| 5 | " | 0.5 | " |
| 6 | " | 0 | " |
| 7 | " | 0 | " |
| non-treated | — | 3 | — |

EXPERIMENTAL EXAMPLE 4

Test for Effect of Controlling Late Blight (*Phytophthora infestans*) on Tomato

A wettable powder as obtained in Example 2 was diluted with and suspended in water in a predetermined concentration and sprayed over young seedlings of tomato plant of the four-leaf-stage (variety:Fukuju No. 2, one seedling/pot, 3 pots/treated plot) cultivated in unglazed pots of 10 cm in diameter. After drying the sprayed leaves, a suspension of spores of *Phytophthora infestans* prepared by washing the inoculated potato tubers with distilled water was sprayed for inoculation over the chemical-sprayed leaves of tomato plant, followed by maintaining at 20°-22° C. for 2 days in a humid house and then allowing to stand in a greenhouse. Four days after the inoculation, the degree of infection was checked on the same standard as in Experimental Example 3 to determine an average degree of infection per seedling. The test results are shown in Table 5 below.

TABLE 5

| Tested Compound No. | Concentration (ppm) | Average Degree of Infection | Phytotoxicity |
| --- | --- | --- | --- |
| 1 | 500 | 0.5 | nil |

TABLE 5-continued

| Tested Compound No. | Concentration (ppm) | Average Degree of Infection | Phytotoxicity |
| --- | --- | --- | --- |
| 2 | " | 0 | " |
| 3 | " | 0 | " |
| 4 | " | 0.5 | " |
| 5 | " | 0 | " |
| 6 | " | 0.5 | " |
| 7 | " | 0 | " |
| non-treated | — | 5 | — |

EXPERIMENTAL EXAMPLE 5

Test for Effect of Controlling Brown Rust (*Puccinia recondita*) on Wheat

A wetting powder, as obtained in Example 2, was diluted with or suspended in water in a predetermined concentration and sprayed over young seedlings of wheat of the three-leaf-stage (variety: Norin No. 64, 16 seedlings/pot) cultivated in unglazed pots of 10 cm in diameter. After drying the sprayed leaves, a suspension of spores of *Puccinia recondita* obtained by washing the inoculated wheat with distilled water was sprayed for inoculation, followed by maintaining under high humidity conditions at 20°-25° C. for 24 hours. Thereafter, the pot was allowed to stand in a greenhouse. Seven days after the inoculation, 10 seedlings were checked on the degree of infection to determine an average degree of infection per leaf.

Check Standard:

| Degree of Infection | Degree of Disease |
| --- | --- |
| 0 | Not infected at all. |
| 0.5 | Infected to a degree that the rate of infected area is below 5%. |
| 1 | Infected to a degree that the rate of infected area is between 5-10%. |
| 2 | Infected to a degree that the rate of infected area is between 10-30%. |
| 3 | Infected to a degree that the rate of infected area is above 30%. |

The test results are shown in Table 6 below.

TABLE 6

| Tested Compound No. | Concentration (ppm) | Average Degree of Infection | Phytotoxicity |
| --- | --- | --- | --- |
| 1 | 500 | 0 | nil |
| 2 | " | 0 | " |
| 3 | " | 0 | " |
| 4 | " | 0 | " |
| 5 | " | 0 | " |
| 6 | " | 0 | " |
| 7 | " | 0 | " |
| non-treated | — | 3 | — |

EXPERIMENTAL EXAMPLE 6

Test for Effect of Controlling Grey Mold (*Botrytis cinerea*) on Cucumber

A wettable powder, as obtained in Example 2, was diluted with and suspended in water in a predetermined concentration and sprayed over leaves of cucumber of the two-leaf-stage (variety: Sagami Hanjiro, one seedling/pot, 3 pots/treated pot) cultivated in unglazed pots of 10 cm in diameter. After drying the sprayed leaves, a agar slice of a disc form (with a diameter of 5 mm)

which contained grey mold which had been cultured at 20° C. for 5 days with use of a sugar-added potato juice agar medium was directly deposited on an approximately central portion of each sprayed leaf to inoculate the disease mold. Five days after the inoculation, the seedlings were kept in a humid house at 22°-23° C. for 5 days. The degree of infection was checked on the following standard basis to determine an average degree of infection.

Check Standard:

| Degree of Infection | Degree of Disease |
| --- | --- |
| 0 | Not infected. |
| 0.5 | Infected beneath or around the inoculated mold-containing agar piece. |
| 1 | Infected to below 20% of the inoculated leaf area. |
| 2 | Infected to 20-40% of the inoculated leaf area. |
| 3 | Infected to 40-60% of the inoculated leaf area. |
| 4 | Infected to 60-80% of the inoculated leaf area. |
| 5 | Infected to more than 80% of the inoculated leaf area. |

The tested results are shown in Table 7 below.

TABLE 7

| Tested Compound No. | Concentration (ppm) | Average Degree of Infection | Phytotoxicity |
| --- | --- | --- | --- |
| 1 | 500 | 0 | nil |
| 2 | " | 0 | " |
| 3 | " | 0 | " |
| 4 | " | 1 | " |
| 5 | " | 0 | " |
| 6 | " | 0 | " |
| 7 | " | 0.5 | " |
| non-treated | — | 5 | — |

EXPERIMENTAL EXAMPLE 7

Test for Effect of Controlling Downy Mildew (*Plasmopara viticola*) on Grape

A wettable powder, as obtained in Example 2, was diluted with and suspended in water in a predetermined concentration and sprayed over a potted young grape tree (variety: Koshu) so that both sides of the leaves were adequately wetted, followed by allowing to stand in a house having a polyvinyl chloride film covering. Four days after the spraying, the leaves were cut off from the sprayed tree, which were sprayed for inoculation with a suspension of spores of *Plasmopara viticola* obtained by washing the inoculated grape leaves with distilled water, followed by maintaining under high humidity conditions at 18°-23° C. Ten days after the inoculation, the degree of infection was checked with regards to three leaves/plot to determine an average degree of infection per leaf on the following standard basis.

Check Standard:

| Degree of Infection | Degree of Disease |
| --- | --- |
| 0 | Not infected. |
| 0.5 | Infected to below 10% of the leaf area. |
| 1 | Infected to 10-25% of the leaf area. |
| 2 | Infected to 25-50% of the leaf area. |
| 3 | Infected to 50-75% of the leaf area. |
| 4 | Infected to more than 75% of the leaf area. |

The test results are shown in the following Table 8.

TABLE 8

| Tested Compound No. | Concentration (ppm) | Average Degree of Infection | Phytotoxicity |
| --- | --- | --- | --- |
| 1 | 500 | 0 | nil |
| 2 | " | 0 | " |
| 3 | " | 0 | " |
| 4 | " | 0 | " |
| 5 | " | 0 | " |
| 6 | " | 0 | " |
| 7 | " | 0 | " |
| non-treated | — | 4 | — |

What is claimed is:

1. An agricultural and horticultural fungicide composition comprising an effective amount of at least one of N-benzoyl-N'-halogenoalkylidenehydrazine derivatives of the formula:

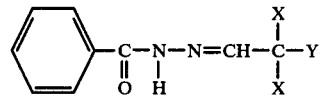

wherein
X represents an atom of chloride or bromine, and
Y is a member selected from the group consisting of hydrogen, fluorine, chlorine, bromine, methyl and 1-chloroethyl, provided that when X is chlorine, Y is one of the above-defined members other than chlorine, and an agriculturally and horticulturally acceptable carrier.

2. A process for preparing N-benzoyl-N'-halogenoalkylidenehydrazine derivatives expressed by the general formula:

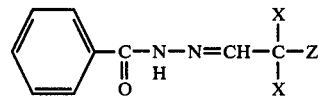

wherein
X represents chlorine or bromine, and
Z represents fluorine, chlorine or bromine characterized by bringing a compound of the general formula:

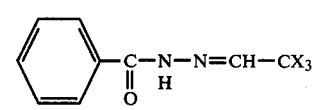

wherein X is as defined above, to reaction with a substance serving as a base to undergo the dehydrohalogenation reaction and subjecting the resulting intermediate to an addition reaction with a hydrogen halide H—Z, wherein Z is as defined above, other than the hydrogen halide removed by the dehydrohalogenation.

* * * * *